(12) United States Patent
Krejci et al.

(10) Patent No.: US 6,407,148 B1
(45) Date of Patent: Jun. 18, 2002

(54) METAL-FREE DENTAL FILLING SYSTEM AS A SUBSTITUTE FOR AMALGAM

(75) Inventors: Daniela Krejci; Ivo Krejci, both of Coppet; Felix Lutz, Meilen, all of (CH)

(73) Assignee: 3M Espe AG, Seefeld (DE)

( * ) Notice: Subject to any disclaimer, the term of this patent is extended or adjusted under 35 U.S.C. 154(b) by 0 days.

(21) Appl. No.: 09/554,442

(22) PCT Filed: Nov. 12, 1998

(86) PCT No.: PCT/IB98/01798

§ 371 (c)(1),
(2), (4) Date: May 15, 2000

(87) PCT Pub. No.: WO99/25309

PCT Pub. Date: May 27, 1999

Related U.S. Application Data
(60) Provisional application No. 60/066,128, filed on Nov. 21, 1997.

(30) Foreign Application Priority Data

Nov. 13, 1997 (DE) .......................................... 197 50 319

(51) Int. Cl.⁷ .............................................. A61K 6/083
(52) U.S. Cl. ........................ 523/116; 523/115; 106/35; 522/908; 433/228.1
(58) Field of Search ........................ 106/35; 433/228.1; 523/116, 117, 118, 115; 522/908

(56) References Cited

U.S. PATENT DOCUMENTS

| 4,425,094 A | 1/1984 | Tateosian et al. ......... 433/228.1 |
| 4,685,969 A | 8/1987 | Schmid et al. ........... 433/228.1 |
| 4,872,936 A | 10/1989 | Engelbrecht ................ 523/116 |
| 5,089,051 A | 2/1992 | Eppinger et al. ........... 523/116 |
| 5,213,615 A | 5/1993 | Michl .......................... 106/35 |
| 5,824,720 A | 10/1998 | Nowak et al. .............. 523/116 |
| 5,849,270 A | 12/1998 | Podszun et al. ............ 523/118 |

FOREIGN PATENT DOCUMENTS

| DE | 36 34 697 | 4/1988 |
| DE | 44 45 266 | 6/1996 |
| DE | 196 03 577 | 8/1997 |
| EP | 0 088 527 | 9/1983 |
| EP | 0 423 430 | 4/1991 |

OTHER PUBLICATIONS

Database WPI, Section Ch, Week 8825, Derwent Publications Ltd., London, GB; Class A96, AN 88–275902 XP002103573 & JP 63 203 604 A (Tokuyama Soda KK), Aug. 23, 1988 (See Abstract).

Primary Examiner—Peter Szekely
(74) Attorney, Agent, or Firm—Crowell & Moring LLP

(57) ABSTRACT

A metal free dental filling system is provided which prevents the transmission of destructive forces from the shrinking filling material to the sealed dental hard tissue. The system prevents the transmission of destructive forces by making the bond of the cured adhesive sealant to the dental hard tissue, i.e., the enamel, dentin, and root cement, substantially stronger than the bond of the cured adhesive sealant to the filling material. An intermediate layer material may be arranged between the dental filling material and the cured adhesive sealant. If an intermediate layer is used, the bond between the dental hard tissue and the cured adhesive sealant is much stronger than the bond between the cured adhesive sealant and the intermediate layer in order to ensure that substantially no destructive forces are transmitted from the shrinking filing material to the cured adhesive material on the dental hard tissue. The intermediate layer may be removed prior to application of the filling material.

23 Claims, No Drawings

METAL-FREE DENTAL FILLING SYSTEM AS A SUBSTITUTE FOR AMALGAM

CROSS REFERENCE TO RELATED APPLICATIONS

This application claims the priority of the German patent application 197 50 319.5, filed on Nov. 13, 1997, and U.S. provisional application No. 60/066,128 filed on Nov. 21, 1997, the disclosure of said applications is incorporated herein by reference in its entirety.

TECHNICAL FIELD

The present invention relates to a metal-free dental filling system for filling therapy or root filling therapy, respectively, as well as to its use as a substitute for amalgam.

BACKGROUND ART

For tooth restoration in dentistry, three hierarchically ordered goals are pursued, whereby each higher standard is based on the fulfillment of the lower standard or the lower standards.

The partial goal of the lowest standard 1 consists in the conservation of the dental hard tissue and the protection of the pulpa.

Standard 2 is further aiming at restoring the tooth's shape and function.

The purpose of standard 3 is to design the restoration in such a way that it is imperceptible at conversation distance and remain so throughout the stipulated service life.

Amalgams, i.e. mixtures of a silver-tin alloy with liquid mercury, have been used for more than 150 years as standard filling material, in particular for posterior, permanent teeth. When used with adequate operative techniques, amalgam restorations are able to protect the dental hard tissue for years and to restore the tooth's shape as well it's functionality. Thus, amalgam restorations fully satisfy standard 2. In filling therapy with amalgam, a comparatively simple operative technique has evolved that relies on steel matrices and wooden wedges for giving the filling its correct, preferably overhang-free contour at its outer surfaces. Occlusal shaping is carried out by carving. Amalgam fillings are furthermore comparatively cheap. The medium survival rate of amalgam fillings can be 10 years and more.

In recent years, however, amalgams have lost quite some ground as a standard restorative material. The main reasons of this decline are, among others, its controversial toxic and allergenic potential, its environmental impact and its lack of tooth color. As a consequence, it was necessary to search for materials or material systems that could be used to replace amalgam for posterior teeth, in particular for permanent teeth and stress-bearing restorations. This resulted in two material or system groups differing in their purpose, namely amalgam alternatives and amalgam substitutes.

Amalgam alternatives have to suffice standard 3 and not only have to guarantee the conservation of the dental hard tissue as well as shape and function of the restored tooth over a long time, but they also must be and remain imperceptible at normal conversation distance. This group of materials in particular comprises composite fillings and composite or ceramic work-pieces. This not only requires tooth color, but also a stress resistant, perfect marginal adaptation. With fillings, the latter is achieved by using a rather complex operative technique, with work-pieces by high accuracy in conjunction with efficient adhesive or combined adhesive/luting systems.

In contrast to this, an amalgam substitute has to satisfy standard 2 just as amalgam does; in addition to this, the operative technique should be simple for cost reasons and be as close as possible to the known amalgam technique, i.e. it should be possible to work with steel matrices and wooden wedges, to use a simple incremental technique and, if light curing materials are used, irradiation from an occlusal direction should suffice.

Various amalgam substitute systems are known:

DE-196 03 577 A1 relates to an adhesive system, wherein a gap free connection between the plastic filling material and the dental hard tissue is aimed at. In such a system, the bond between dental hard tissue and filling material is excellent, such that in case of adhesive failures, continuity fractures occur in the dental hard tissue or in the restorative material. This means that no caries protection is provided along these marginal openings if they run in the dental hard tissue.

DE 195 44 670 describes an adhesive system that does not harden by radical polymerization but rather as a product of condensation. In this way, an oxygen-inhibited surface layer is to be avoided. Thus, however, the adhesive may be better suited than usual, radically polymerizing sealants for sealing caries. In the application as an adhesive, where, according to the inventor, the prevention of margin gap formation is again aimed at, cohesive failure results in the dentin and in the enamel. Hence, this system is unable to reliably protect the dental hard tissue. With comparatively frequent adhesive failure, the enamel is not protected at all in the area of the marginal openings, which are therefore not desired at all. In dentin, a partial, erratic, unpredictable protection is to be expected where the bond happens to break between the adhesive and the filling material and adhesive islands remain on the dental hard tissue. The described system therefore provides no safe and complete protection of the enamel or dentin, and it also belongs to the category of the adhesive systems aiming at a total bond between the dental hard tissue and the restorative material.

EP 0 423 430 describes a dentin-adhesive system using a primer and a bond on dentin. Again, it is aimed at a total leakage-free bond between dental hard tissue and restorative material.

EP 0 088 527 describes an enamel conditioner designed to generate a better bond between the enamel and the restorative material than it used to be the case upon the usual etching process by means of phosphoric acid.

DE 34 14 163 relates on a dentin primer and describes a dentin bonding system working with a primer and a bond on dentin, wherein again a total leakage-free bond between dental hard tissue and restorative material is desired.

None of the adhesive systems according to the state of the art, however, uses enamel and dentin bonding selectively for protection and adhesive sealing of the dental hard tissue, while selectively eliminating the requirement of a bond between the shrinking restorative material and the sealed dental hard tissue.

The adhesive systems according to the state of the art are fully unsatisfactory when being used in combination with amalgam substitutes and the corresponding operative techniques, because unpredictably located fractures in the restorative material, the interface between restorative material and adhesive, within the adhesive, at the interface between the adhesive and the dental hard tissue and/or within the dental hard tissue can occur. Fractures at the interface between the adhesive and the dental hard tissue and within the dental hard tissue are particularly damaging. A reliable protection cannot be achieved using the required simple placement techniques and currently available adhesive systems.

Investigations have shown that fillings made of materials presently used as amalgam substitutes are visible after a short period of time especially when occlusally loaded. Such materials include amalgam substitutes in combination with an adhesive system such as composite-adhesive or compomer adhesive systems, i.e., polyacid-modified composites, as well as composite adhesive systems specifically developed as amalgam substitutes. Sometimes within months, from 60% to 95% of the total margin length of the filling is visible resulting in both marginal discoloration and a high risk for secondary caries in medium time range caries diagnostics.

While marginal discoloration may be acceptable within the requirements of operative standard 2, the high risk for secondary caries with fillings of the known material combinations mentioned above, cannot satisfy operative standard 1, i.e., tooth conservation can not be achieved over a medium time range. Thus, materials presently used as amalgam substitutes should only be used as temporary fillings.

The reason for the failure of the amalgam substitute materials according to the state of the art lies in the fact that such materials usually shrink by 2.5 to 4.5 volume percent during the curing process. The resulting stress build-up damages the bonds as generated by the adhesive systems according to the state of the art and exceeds the cohesive strength of the dental hard tissue, especially in the enamel, and of the filling material itself. Under stress, non-predictable continuity fractures occur, namely fissures in the enamel and, more rarely, in the dentin, a breaking of the bond between dental hard tissue and adhesive system, within the adhesive system, at the interface between adhesive system and filling, and within the filling. Even though an adhesive system is used, unprotected, adhesive free areas of dental hard tissue are exposed, either due to cohesive fractures within the dental hard tissue or due to a breaking of the bond between the adhesive system and the dental hard tissue.

DISCLOSURE OF THE INVENTION

Hence, it is a general object of the invention to provide a dental filling system that avoids at least part of the above disadvantages and problems.

In particular, it was an aim of the present invention to provide an amalgam substitute, which fulfills the above partial goals 1 and 2 as well as, possibly, 3.

This object is achieved according to claim 1. Preferred embodiments are described in the dependent claims.

The metal free, dental filling system for the filling therapy of cavities or for the filling therapy of root canals according to the present invention comprises a) a dental filling material for cavities or root canals, as well as b) an adhesive, curing or self-curing sealant for the dental hard tissue, c) wherein the adhesive bond of the cured adhesive sealant to the dental hard tissue, i.e., the enamel dentin, and root cement, is substantially stronger than to the cured filling material such that substantially no destructive forces are transmitted from the shrinking filling material to the adhesive sealant.

In an especially preferred embodiment the filling system according to the invention comprises an intermediate layer material d), which is suitable to be arranged between the dental filling material a) and the sealant b), wherein the adhesive bond between the cured adhesive sealant b) to the dental hard tissue is much stronger than to the intermediate layer material d), such that substantially no destructive forces are transmitted from the shrinking filling material to the adhesive sealant.

Preferably, said intermediate layer material d) is removable before application of the filling material.

In an especially preferred embodiment, substantially no adhesive bond is formed between the cured sealant b) to the filling material a) or, if applicable, to the intermediate layer d), respectively, such that during the curing no destructive forces at all are transmitted from the shrinking filling material a) and/or the intermediate layer material d) to the adhesive sealant b).

Hence, in contrast to the known state of the art the present invention does not aim at protecting the dental hard tissue by a perfect bond to the filling material. The present invention rather provides an isolating, selective adhesive seal of the dental hard tissue, thereby generating the desired protection in the area of the margin gaps.

Preferably, the desired separation or, compared to the destructive stress build-up within the filling, the weak, no stress transferring bonds between the sealant and the filling material are achieved by making known adhesive coatings unable to co-polymerize or lock by a suitable choice of monomers, admixtures or curing methods. Alternatively, instead of using a known adhesive system, an adhesive system is used that adheres to the enamel and dentin, forms a coating, is chemically and physically resistant but does not form a mechanical or chemical bond to the filling system that might endanger its own bond to the hard dental material.

Using the system according to the invention, the dental hard tissue remains free of fractures and is protected against caries and erosive processes throughout the stipulated service life of the filling. The amalgam substitute according to the invention therefore meets standard 2 by a complete prevention of the risk of secondary caries and by preserving the dental hard tissue, while shape and function of the tooth are restored by the filling material.

MODES FOR CARRYING OUT THE INVENTION

The main object of the present invention is a dental filling system that that eliminates the need for a total bond from the sealant b) for the dental hard tissue to the filling material a) or the intermediate layer material d), respectively. An isolated, selective adhesive sealing of the dental hard tissue can be reached as follows:

A) A transmission of shrinking-forces can be avoided by preventing mechanical interlocking and homo or co-polymerization between the dental filling material a) and, if present, the intermediate layer material d) on the one hand, as well as the adhesive sealant b) for the dental hard tissue on the other hand. This can e.g. be achieved by entirely coating the sealant b) by a separation layer. For this purpose, painting materials, such as zinc oxide-Eugenol, said compound being known to those skilled in the art, barrier materials, such as powders or powder coatings, or glycerolacetate-based isolating gels, or primers, e.g., silicon-organic compounds.

B) The undesired transmission of the shrinking forces from the filling material to the adhesive sealant can be further prevented by a reduction of the free radicals at the surface of the radically polymerizing sealant. In a further preferred embodiment, the undesired transmission of the shrinking-forces is therefore prevented by the fact the hardened adhesive sealant b) has a low free radical content and is therefore not apt for co-polymerization.

It is especially preferred that the hardened sealant b) is even unable to undergo homo- and/or co-polymerization.

The ability for co-polymerization of the components a), b) and d) can e.g. be affected and weakened by admixing of BisGMA (2,2-Bis[4-(2-hydroxy-3-methacryloxypropoxy) phenyl] propane) bicarbonate (of the Bayer Company) or photo-initiators in higher concentrations, or by coating the sealant b) with an arbitrary air blocker as known to the person skilled in the art before light curing for preventing the build-up of an oxygen-inhibited surface layer.

On the other hand, a reduction of the free radicals at the surface of a radically polymerizing sealant can also be reached by a suitable choice of the monomer systems.

C) In a further preferred embodiment a transmission of shrinking-forces is reduced or diminished by using filling materials d) and adhesive sealants b) of different polarity, notably for suppressing wetting. It is especially preferred to use a hydrophilic or amphiphilic sealant for the dental hard tissue and a strongly hydrophobic filling system. Particularly preferred is thereby a sealant b) being hydrophilic or amphiphilic, whereby the filling material a) is strongly hydrophobic, e.g., Etch & Prime 3.0 or Prime & Bond NT (of the Dentsply company) combined with Adaptic II (Johnson & Johnson) or Pertac (Espe company). Also preferred is a sealant b) being hydrophobic whereas the filling material is strongly hydrophilic, e.g. Visiobond (Espe company) in combination with PhotacFil (Espe company) or Ketac (Espe company) Bond.

D) Especially, if the dental filling material a) is a methacrylated substance, the adhesive sealant b) has a separating effect in respect to the filling material a) due to a different polymerization that does not allow a co- or homo-polymerisation of di- or polyacrylatesystems. This prevents a shrinking-force transmitting bond between the adhesive sealant and the filling material. Preferred sealants for the dental hard tissue are selected from the group comprising water glass, silica ester hydrolysates, polymerizable silane compounds, natural resin varnishes, cyanate based varnishes, epoxide resins, epoxidated soy oil or epoxy-modified silicones. They can preferably be selected as follows:

water glass: e.g. a water glass glue in colloidal solution of potassium or sodium silicate, wherein the setting takes place, e.g. through evaporation of the water share.

silica ester hydrolysates: Through the preparation of partial hydrolysates of silica ester hydrolysates, solid resin coatings can be achieved. The mode of preparation of such a coating could be e.g. vinyltriethoxysilane 12% per weight, silica ester TES (tetraethoxy silane) (Dynamit Nobel) 34% per weight, phosphoric acid 0.3% per weight dissolved in acetone. After the evaporation of the solvent, clear, hard, shining hydrophobic films are formed. The adhesion to substrates such as dentin and enamel can be adjusted by means of metal acetylacetonates.

polymerizable silane compounds: preferably silanes being modified with epoxide- or methacrylate groups. The mentioned reactive silane monomers could contain metal complexes having an affinity to the dentin or the enamel, e.g. compounds with calcium, fluorine or other halides;

epoxy resins: As an example the epoxide-modified vinylester resins, polyester resins, vinyletherresins or bisphenol-A-epoxid resin (Dow Corning) Dercane Oli-gomer; vectomer-vinylether oligomeres, ISP= vinylether (ISP company), CIBA Araldit types (Ciba-Geigy company); Union Carbide cycloaliphatic epoxides are to be mentioned. Depending on their modification, said raw materials could be polymerized through radical or ionic initiation, thus providing 2-component systems hardening chemically, e.g. following to the preparation comprising the component A: bisphenol-A-epoxy resins (D.E.R. 335 Dow Corning); Cumene hydroperoxide and component B: bisphenol-A-epoxyresin, silane Z-6020 (Dow Corning) and triethanolamine. Correspondingly the formulations that harden upon light exposure are conceivable with light in the visible or ultra-violet range, e.g. following to the preparation Vectomer 2010 urthan oligomer (of the Vectomer company) 45% per weight, monomer 4010 15% per weight, Rapicure CHVE (of the ISP company) monomer 39% by weight (1,4-cyclohexane-dimethanole-divinylether), cationic initiator UVI-6974 1% per weight.

natural resin varnishes: Through hydrophobic natural resin varnishes forming films, dense, hydrophobic coatings could be achieved, e.g. following the preparation of Cophonium 12% per weight, Shellac 25% per weight, gum arabic 8% per weight, Cellulose 5% per weight and Alkohol DAB (Deutsches Arzneibuch) to make 100%.

epoxidated soy oils: They are cross-linkable through cationic or radical initiation, e.g. Henkel Edenol types; further examples for reactive oligomers are cyracure oligomeres (Union Carbide), cycloaliphatic epoxide resins like UVR 61110 (Dow Corning), i.e. 3,4-epoxycyclohexylmethyl-3,4-epoxycyclohexane-carboxylate, or UVR 6128 (Dow Corning), i.e. bis-(3,4 epoxycyclohexyl-adipate or UVR 6216 (Dow Corning), i.e. 1,2-epoxyhexadecane.

methacrylic or epoxy-modified silicones (e.g. of Goldschmidt, Wacker, Mitsubishi) as well as methacryl-modified gelatines and cellulose esters also display good film forming properties: they could also serve as film-forming carrier materials for a variety of active agent, like fluorides or antiseptic or bactericidal additives. The desired separation effect is notably achieved by employing 2 different synthesis forms. Said process could be achieved through different cross-linkage mechanisms, like the chemical hardening, the light-induced hardening, the radical- or cationic induced hardening, cross-linking through radical condensation etc.

The filling materials a) comprise plastics, composites, compomers, ormaceres, ceromers, polyglasses, glass ionomer cements, carboxylate cement, phosphate cement, EBA (ethoxybenzoic acid) cement (ESPE company) or guttapercha, or materials consisting thereof. These materials are preferably photo curing, chemically curing, dually curing, heat curing or thermoplastic.

The above mentioned compounds are commercially available and are generally known by persons skilled in the art.

The sealants b) for the dental hard tissue exhibit a good bond with the dental hard tissues. They form a leakage-free and gap-free, closed, mechanically and chemically resistive protective layer and, if possible, release (as a "smart material") caries protective agents, i.e. they release plaque-suppressing or caries-protective agents permanently or upon request, such as fluorides, chlorhexidine, triclosan, calcium or hydoxyl-ions. Preferably used sealants for the dental hard tissue are photo hardening, chemically hardening, dually curing, heat curing or thermoplastic or they cure using the principles of contact glues.

In a highly preferred embodiment the dental filling material a) is photo hardening (i.e. hardening upon exposure to light of a suitable wave-length) and the sealant b) for the dental hard tissue is chemically hardening.

In another preferred embodiment the dental filling material a) is chemically curing and the sealant b) for dental hard tissue is photo curing.

The adhesive sealant b) can further also be used as a base material, as a proximal sealant or as a fissure sealant.

Using the filling system presented here, it is possible to prepare fillings that are metal free and preferably tooth colored with a required simple, economical operative technique corresponding to the general skill of the dentist. Such filling systems are true amalgam substitutes because they not only restore the tooth's shape and function but also protect the same against caries and erosion. Analogously, such systems can also be used for root fillings.

A further aspect of the present invention is a method for filling therapy of cavities or root canals by using one of the dental filling systems described above.

The present invention shall, in the following be illustrated by the following examples, which are not to be construed as limiting the scope of the invention.

EXAMPLE 1

The following sealants are set forth for the purpose of the ensuing creation of a filling system:

| a) sealing through radical crosslinking: | |
|---|---|
| BisGMA or Urethane DMA (dimethacrylate) | 49.0% per weight |
| hydroxyfunctionalized methacrylate | 29.5% per weight |
| acid modified polymethacrylate | 20.0% per weight |
| photoinitiator system | 1.5% per weight |
| b) sealing through low-shrinking cationic cross-linking | |
| epoxy functionalized oligomer | 70% per weight |
| epoxy functionalized polyol | 27% per weight |
| cationic initiator | 3% per weight |
| c) low shrinking composite by cationic cross-linking: | |
| epoxy functionalized resin mixture | 25% per weight |
| x-ray active Ba/Al-borosilicate glass <2.0 micron | 75% per weight |

EXAMPLE 2

A cavity is sealed upon using the composition a) of example 1, and thereafter it is filled with the low-shrinking composite c) of example 1 and is finally irradiated with a polymerisation lamp for about 60 seconds. The filling thus obtained does not form any bond with the sealant having been formed upon radical cross-linking and forms therefore a dense, strainable and durable filling system due to the minimal shrinkage. There is essentially no tension transfer to the dental hard tissue.

EXAMPLE 3

Cavities, tiny lesions or fissures are sealed and cured (hardened) with a radically cross-linking sealant according to item a) of example 1). Thereafter the sealing resin according to item b) of example is applied and irradiated for about 60 seconds. The result is a stress-free sealing of said cavity, lesion or fissure. Due to the high conversion rate of the cationic cross-linking system of item b) of example 1, an inhibition-free layer is the result. Plaque, beverages like tea, coffee could not cause any discolorations. The chemical degradation does intervene only to a minor extent. The mechanical abrasion could also be diminished.

EXAMPLE 4

A cavity is filled with a composite c) of example 1). Due to the high conversion rate of the preceding cationic sealing, no chemical bond is generated between the sealant and the filling material. The result is a solid, stress-resistant filling on the one hand and a well-protected adhesive sealing of the dental hard tissue on the other hand. Due to the absence of material shrinkage-related stress, the comfort for carrying such a restoration is to be underlined.

EXAMPLE 5

Conventional fillings having been placed with commercially available composites or compomers (i.e. acid-modified composites) could also be sealed-off by means of a cationic cross-linking sealant according to item b) of example 1, thus avoiding secondary caries resulting from shrinkage of the filling material.

While there are shown and described presently preferred embodiments of the invention, it is to be distinctly understood that the invention is not limited thereto but may be otherwise variously embodied and practiced within the scope of the following claims.

What is claimed is:

1. A metal free dental filling system for the filling therapy of cavities or root canals, characterized in that it comprises:
   a) a dental filling material for cavities or root canals, and
   b) an adhesive, curable or self-curing sealant for the dental hard tissue,
   c) wherein the adhesive bond from the adhesive sealant to the dental hard tissue is stronger than the adhesive bond from the adhesive sealant to the cured filling material, such that substantially no destructive forces are transmitted from the shrinking filling material to the adhesive sealant.

2. The dental filling system of claim 1, wherein it further comprises an intermediate layer material arranged between the dental filling material and the adhesive sealant, wherein the adhesive bond from the adhesive sealant to the dental hard tissue is stronger than the adhesive bond from the adhesive sealant to the intermediate layer material, such that substantially no destructive forces are transmitted from the shrinking filling material to the adhesive sealant during curing.

3. The dental filling system of claim 2, wherein the intermediate layer material is removable before the application of the filling material.

4. The dental filling system of claim 1, wherein substantially no adhesive bond is formed between the cured adhesive sealant and the filling material or the adhesive sealant and the intermediate filling material, such that transmission of the destructive forces from the shrinking filling material or the intermediate layer material to the adhesive sealant during curing is prevented.

5. The dental filling system of claim 1, wherein the bonds between the adhesive sealant and the dental filling material or the adhesive sealant and the intermediate layer material do not show a mechanical interlocking or bonding to each other caused by homo- or co-polymerization.

6. The dental filling system of claim 5, wherein the mechanical interlocking or bonding by homo- or co-polymerization is prevented by fully coating the adhesive sealant with a separation layer selected from the group consisting of painted materials, barrier materials, and glycerol-acetate containing isolating gels or primers.

7. The dental filling system of claim 1, wherein the free radicals at the surface of the cured adhesive sealant are reduced such that the adhesive sealant is not apt for co- or homo-polymerization with the filling material or the intermediate layer material.

8. The dental filling system of claim 7, wherein the cured adhesive sealant is unable to undergo homo- and/or co-polymerization at the common interface surfaces with the filling material or the intermediate layer material.

9. The dental filling system of claim 7, wherein co-polymerization of the adhesive sealant and the filling material or the adhesive sealant and the intermediate layer material is weakened by an admixture of 2,2-bis[4-(2-hydroxy-3-methacryloxypropoxy)phenyl] propane (BisGMA) bicarbonate or an excess of photo-initiators, or by coating the adhesive sealant with an air blocker prior to light-curing for preventing the build-up of an oxygen inhibited surface layer.

10. The dental filling system of claim 1, wherein the filling material, the intermediate layer material, and the cured adhesive sealant are differently polar for suppressing wetting.

11. The dental filling system of claim 10, wherein the cured adhesive sealant is hydrophilic or amphiphilic and the filling material is hydrophobic.

12. The dental filling system of claim 1, wherein the filling material is a methacrylated substance and the adhesive sealant does not allow co- or homo-polymerization of di- or polyacrylate systems such that a shrinking-force transmitting bond between the sealant and the filling material is prevented.

13. The dental filling system of claim 12, wherein the adhesive sealant is selected from the group consisting of water glass, silica ester hydolysates, polymerizable silane compounds, natural resin varnishes, cyanate containing varnishes, epoxy resins, epoxidated soy oils, and epoxy modified silicones.

14. The dental filling system of claim 1, wherein the dental filling material and/or the sealant are photo hardening, chemically hardening, dually hardening, heat hardening, thermoplastic, or, wherein the dental filling and/or the sealant harden upon contact with a surface containing the same material.

15. The dental filling system of claim 14, wherein the filling material is light curing and the sealant is chemically self-curing.

16. The dental filling system of claim 14, wherein the filling material is chemically self-curing and the sealant is light curing.

17. The dental filling system of claim 1, wherein the filling material is selected from the group consisting of plastics, composites, ceromers, polyglasses, glass ionomer cements, carboxylate cement, phosphate cement, ethoxybenzoic acid (EBA) cement, and guttapercha.

18. The dental filling system of claim 1, wherein the adhesive sealant releases plaque-suppressing or cariesprotective agents.

19. The dental filling system of claim 1, wherein the dental fillings are tooth colored.

20. A method for therapeutic and restorative treatment of cavities and for therapeutic and restorative root canals comprising the acts of filling a cavity or root canal of a patient according to the dental filling system of claim 1.

21. The dental filling system of claim 6, wherein said painted materials include zinc oxide-Eugenol.

22. The dental filling system of claim 6, wherein said barrier materials include powders or powder coatings.

23. The dental filling system of claim 6, wherein said glycerol-acetate containing isolating gels or primers include silicone-organic compounds.

* * * * *